United States Patent
Jinkerson et al.

(10) Patent No.: US 7,691,918 B2
(45) Date of Patent: Apr. 6, 2010

(54) INTRAOCULAR LENSES WITH UNIQUE BLUE-VIOLET CUTOFF AND BLUE LIGHT TRANSMISSION CHARACTERISTICS

(75) Inventors: David L. Jinkerson, Benbrook, TX (US); Joseph I. Weinschenk, III, Fort Worth, TX (US); Mutlu Karakelle, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/871,411

(22) Filed: Oct. 12, 2007

(65) Prior Publication Data

US 2008/0090937 A1    Apr. 17, 2008

Related U.S. Application Data

(60) Provisional application No. 60/851,666, filed on Oct. 13, 2006, provisional application No. 60/889,131, filed on Feb. 9, 2007.

(51) Int. Cl.
| | |
|---|---|
| G02B 1/04 | (2006.01) |
| C08F 290/04 | (2006.01) |
| G02C 7/04 | (2006.01) |
| G02C 7/10 | (2006.01) |

(52) U.S. Cl. .................. 523/106; 523/107; 351/160 R; 351/162; 351/163

(58) Field of Classification Search ................ 523/106, 523/107, 108; 526/259; 351/160 R, 160 H, 351/162, 163
See application file for complete search history.

(56) References Cited

U.S. PATENT DOCUMENTS

| | | | |
|---|---|---|---|
| 4,390,676 A | 6/1983 | Loshaek | |
| 4,528,311 A * | 7/1985 | Beard et al. ................... 524/91 |
| 4,611,061 A | 9/1986 | Beard et al. | |
| 4,716,234 A | 12/1987 | Dunks et al. | |
| 4,795,461 A | 1/1989 | Lindqvist et al. | |
| 4,803,254 A | 2/1989 | Dunks et al. | |
| 5,147,902 A | 9/1992 | Ichikawa et al. | |
| 5,235,358 A | 8/1993 | Mutzhas et al. | |
| 5,470,932 A * | 11/1995 | Jinkerson .................... 526/312 |
| 5,528,322 A | 6/1996 | Jinkerson | |
| 5,543,504 A * | 8/1996 | Jinkerson .................... 534/856 |
| 5,637,726 A | 6/1997 | Collins et al. | |
| 5,662,707 A | 9/1997 | Jinkerson | |
| 5,693,095 A | 12/1997 | Freeman et al. | |
| 5,861,031 A | 1/1999 | Namdaran et al. | |
| 6,166,218 A | 12/2000 | Ravichandran et al. | |

(Continued)

FOREIGN PATENT DOCUMENTS

CN     1727338     2/2006

(Continued)

OTHER PUBLICATIONS

AcrySof Natural Product Monograph, Alcon Laboratories, Inc., 2004.

(Continued)

*Primary Examiner*—Mark Eashoo
*Assistant Examiner*—Michael Pepitone
(74) *Attorney, Agent, or Firm*—Scott A. Chapple (57) ABSTRACT

Disclosed are ophthalmic device materials having improved light transmission characteristics. The materials contain a combination of certain UV absorbers and blue-light absorbing chromophores.

16 Claims, 2 Drawing Sheets

U.S. PATENT DOCUMENTS

| | | | |
|---|---|---|---|
| 6,210,438 B1 * | 4/2001 | Sheets et al. | 623/6.56 |
| 6,242,551 B1 | 6/2001 | Tsuzuki et al. | |
| 6,310,215 B1 | 10/2001 | Iwamoto | |
| 6,320,008 B2 | 11/2001 | Tsuzuki et al. | |
| 6,353,069 B1 * | 3/2002 | Freeman et al. | 526/319 |
| 6,528,602 B1 * | 3/2003 | Freeman et al. | 526/259 |
| 6,653,422 B2 * | 11/2003 | Freeman et al. | 526/259 |
| 6,657,032 B2 * | 12/2003 | Vanderbilt | 526/320 |
| 6,703,466 B1 * | 3/2004 | Karakelle et al. | 526/259 |
| 6,806,337 B2 | 10/2004 | Schlueter et al. | |
| 6,846,897 B2 | 1/2005 | Salamone et al. | |
| 6,852,793 B2 | 2/2005 | Salamone et al. | |
| 6,872,793 B1 | 3/2005 | Schlueter | |
| 6,878,792 B2 | 4/2005 | Ichinohe | |
| 6,918,931 B2 | 7/2005 | Lai et al. | |
| 7,037,954 B2 | 5/2006 | Baba et al. | |
| 7,067,602 B2 | 6/2006 | Benz et al. | |
| 7,098,283 B2 | 8/2006 | Lai | |
| 7,101,949 B2 | 9/2006 | Salamone et al. | |
| 7,119,210 B2 * | 10/2006 | Schlueter | 548/260 |
| 7,278,737 B2 | 10/2007 | Mainster et al. | |
| 7,326,423 B2 | 2/2008 | Pearson et al. | |
| 2002/0042653 A1 | 4/2002 | Copeland et al. | |
| 2005/0054797 A1 | 3/2005 | Lai | |
| 2005/0054803 A1 | 3/2005 | Lai et al. | |
| 2005/0055090 A1 * | 3/2005 | Lai et al. | 623/5.16 |
| 2005/0055091 A1 | 3/2005 | Lai et al. | |
| 2005/0143812 A1 | 6/2005 | Paul et al. | |
| 2005/0243272 A1 | 11/2005 | Mainster et al. | |
| 2005/0254003 A1 * | 11/2005 | Jani et al. | 351/160 R |
| 2005/0283234 A1 | 12/2005 | Zhou et al. | |
| 2006/0020337 A1 | 1/2006 | Lai et al. | |
| 2006/0020338 A1 | 1/2006 | Lai et al. | |
| 2006/0020340 A1 | 1/2006 | Lai et al. | |
| 2006/0041038 A1 | 2/2006 | Xia | |
| 2006/0096044 A1 | 5/2006 | Miki et al. | |
| 2006/0197067 A1 | 9/2006 | Xia et al. | |
| 2006/0241263 A1 | 10/2006 | Lai | |
| 2006/0241264 A1 | 10/2006 | Lai | |
| 2006/0252844 A1 * | 11/2006 | Mentak | 523/106 |
| 2006/0252850 A1 | 11/2006 | Jani et al. | |
| 2007/0092830 A1 | 4/2007 | Lai et al. | |
| 2007/0092831 A1 | 4/2007 | Lai et al. | |
| 2008/0242818 A1 | 10/2008 | Benz et al. | |

FOREIGN PATENT DOCUMENTS

| | | |
|---|---|---|
| EP | 1 033 590 | 5/2008 |
| JP | 1 299560 | 4/1989 |
| JP | 2005 053058 | 3/2005 |
| JP | 2009 013148 | 1/2009 |
| WO | 00/04848 | 2/2000 |
| WO | 2006/057824 | 6/2006 |
| WO | 2006/119304 | 11/2006 |
| WO | 2006/119328 | 11/2006 |
| WO | 2006/121876 | 11/2006 |
| WO | 2007/050394 | 5/2007 |
| WO | 2007/050395 | 5/2007 |
| WO | 2007/147599 | 12/2007 |

OTHER PUBLICATIONS

Braunstein et al., "A blue-Blocking Intraocular Lens Should be Used in Cataract Surgery," Arch. Ophthalmology, vol. 123, pp. 547-549 (2005).

Mainster et al., "How Much Blue Light should an IOL Transmit?", British J. of Ophthalmology, vol. 87, pp. 1523-1529 (2003).

Mainster et al., "Intraocular Lenses Should block UV Radiation and Violet but Not Blue Light," Arch. Ophthalmology, vol. 123, pp. 550-555 (2005).

Mainster et al., "The Spectra, Classification, and Rationale of Ultraviolet-Protective Intraocular Lenses," American J. of Ophthalmology, vol. 102, pp. 727-732 (1986).

Mainster et al., "violet and blue light blocking intraocular lenses: photoprotection versus phtoreception," British J. of Ophthalmology, vol. 90, pp. 784-792 (2006).

PCT International Search Report for corresponding PCT/US2007/081204 with mailing date Jul. 3, 2008.

PCT Written Opinion for corresponding PCT/US2007/081204 with mailing date Jul. 3, 2008.

Van de Kraats et al., "Sharp cutoff filters in intraocular lenses optimize the balance between light reception and light protection," J. Cataract Refractive Surgery, vol. 33, pp. 879-887 (2007).

Zhao et al., "The effect of chromatic dispersion on pseudophakic optical performance," British J. of Ophthalmology, vol. 91, pp. 1225-1229 (2007).

* cited by examiner

INTRAOCULAR LENSES WITH UNIQUE BLUE-VIOLET CUTOFF AND BLUE LIGHT TRANSMISSION CHARACTERISTICS

This application claims priority to U.S. Provisional Applications, U.S. Ser. No. 60/851,666 filed Oct. 13, 2006 and U.S. Ser. No. 60/889,131 filed Feb. 9, 2007.

FIELD OF THE INVENTION

This invention is directed to improved ophthalmic device materials. In particular, this invention relates to implantable ophthalmic lenses that have improved light transmission characteristics.

BACKGROUND OF THE INVENTION

In the past, benzotriazole UV absorbers, like oMTP (compound 1), have been added to intraocular lens (IOL) materials to provide protection from UV radiation in the environment. Typically, UV absorbers possess a polymerizable moiety, such as vinyl, acrylate or methacrylate functionality in their chemical structure, for covalent incorporation into the IOL material during polymerization. Most of these benzotriazole UV absorbers will provide a UV transmission cut-off of between 1 and 10% in the 390-410 nm range depending on concentration.

Compound 1

More recently, polymerizable yellow dyes have also been added to IOLs to absorb harmful blue light radiation. See, for example, U.S. Pat. Nos. 5,470,932 and 5,543,504. Most yellow dyes absorb blue light over a wide wavelength range and bring about a gradual attenuation of blue light, usually from 500 to 400 nm depending on the concentration of yellow dye used. If a sharper cut-off of the transmission spectrum in the blue-violet region is desired, conventional yellow dyes could not provide a sharp cut-off in that region. See, also, US 2005/0243272, which discloses ophthalmic devices having a highly selective violet light transmissive filter that selectively filters wavelengths between approximately 400 nm to about 450 nm with little or no absorption of wavelengths above 450 nm.

SUMMARY OF THE INVENTION

Ophthalmic device materials particularly suited for use as IOLs, but which are also useful as other ophthalmic devices, such as contact lenses, keratoprostheses, or corneal rings or inlays, have been discovered. These materials comprise a combination of certain UV absorbers and polymerizable yellow dyes. The materials have improved light transmission characteristics compared to the natural human crystalline lens, particularly in the short wavelength blue light region.

By using certain benzotriazole UV absorbers in combination with polymerizable yellow dyes, the light absorption characteristics of IOLs can be altered to provide blue-violet cutoffs (~1% T in 400-430 nm range), and provide transmission that attenuates blue light from 500 to 400 nm. The materials of the present invention have the following light transmission characteristics (based on a rectangular film or "slab" material sample about 0.8-1 mm in thickness). They will have a transmission cut-off within the blue-violet region (400-440 nm) of the UV-Visible spectrum. This blue-violet cut-off is characterized by the wavelengths attained for the 1% and 10% transmission values. Therefore, the preferred blue-violet cut-off wavelengths will be 410 to 430 nm for the 1% T cut-off and from 420 to 440 nm for the 10% T cut-off. These ranges of the preferred blue-violet cut-offs are also provided in Table 1.

The transmission characteristics through the mid-blue light region (440-460 nm) entail most of the transition between high levels of transmitted light (>70%) and absorbed light. The ranges of transmission for 440, 450, and 460 nm are listed in Table 1. Flexibility is allowed in this region to permit the approximation to a young human crystalline lens or to provide maximum protection for the benefit of patients with compromised retinal function.

Finally, the high transmission portion (470-500 nm) is the area of the blue light region where more light is allowed to transmit through the intraocular lens up to the maximum transmission of light possible. This portion of the blue light spectrum is less harmful to the retina than the short wavelength blue-violet light and higher transmission is allowed. The ranges of the preferred characteristics for the high transmission blue light region are also provided in Table 1.

TABLE 1

| | Transmission Characteristics | | |
| --- | --- | --- | --- |
| | | Ranges of Transmission Characteristics* | |
| Blue light region | Transmission Characteristic | Minimum value | Maximum value |
| Blue-violet cut-off | 1% T | 410 nm | 430 nm |
| | 10% T | 420 nm | 440 nm |
| Mid-blue transition region | 440 nm | 10% T | 75% T |
| | 450 nm | 28% T | 80% T |
| | 460 nm | 40% T | 85% T |
| High transmission blue light region | 470 nm | 55% T | 95% T |
| | 480 nm | 68% T | 95% T |
| | 490 nm | 80% T | 95% T |
| | 500 nm | 85% T | 95% T |

*These values are determined by UV-Visible measurements in air.

DETAILED DESCRIPTION OF THE INVENTION

Unless indicated otherwise, all component amounts are presented on a % (w/w) basis ("wt. %").

Unless otherwise specified, "cut-off" means the wavelength at which light transmission does not exceed 1%. "1% cut-off" means the wavelength at which light transmission does not exceed 1%. "10% cut-off" means the wavelength at which light transmission does not exceed 10%.

Typical benzotriazole or benzophenone UV absorbers provide a sharp cut-off at wavelengths less than 400 nm for IOL materials, depending on UV absorber concentration. Certain substituted 2-hydroxyphenyl benzotriazole UV absorbers, however, can provide a transmission cut-off in the short wavelength visible (410-430 nm) region of the spectrum and also provide protection from UV radiation (<400 nm). The UV/short wavelength visible light absorbers suitable for use in the ophthalmic device materials of the present invention are represented by formula (I).

(I)

wherein for formula (I)

$R_1$ is a halogen, OH, $C_1$-$C_{12}$ alkyloxy, optionally substituted phenoxy, or optionally substituted napthyloxy, where the optional substituents are $C_1$-$C_6$ alkyl, $C_1$-$C_6$ alkoxy, OH, —$(CH_2CH_2O)_n$—, or —$(CH_2CH(CH_3)O)_n$—;

$R_2$ is a $C_1$-$C_{12}$ alkyl, $(CH_2CH_2O)_n$, $(CH_2CH(CH_3)O)_n$, or $CH_2CH_2CH_2(Si(CH_3)_2O)_mSi(CH_3)_2CH_2CH_2CH_2$;

X is nothing if $R_2$ is $(CH_2CH_2O)_n$ or $(CH_2CH(CH_3)O)_n$, otherwise X is O, $NR_4$, or S;

$R_3$ is nothing, C(=O), C(=O)$C_jH_{2j}$, $C_1$-$C_6$ alkyl, phenyl, or $C_1$-$C_6$ alkylphenyl;

$R_4$ is H or methyl;

$R_5$ is H, $C_1$-$C_6$ alkyl, or phenyl;

$R_6$ is H or $C_1$-$C_{12}$ alkyl;

m is 1-9;

n is 2-10; and j is 1-6.

Preferably in formula (I), $R_1$ is Cl, Br, $C_1$-$C_4$ alkoxy, or phenoxy;

$R_2$ is $C_1$-$C_6$ alkyl;

X is O or $NR_4$;

$R_3$ is C(=O) or $C_1$-$C_6$ alkylphenyl;

$R_4$ is H or methyl;

$R_5$ is H; and $R_6$ is $C_4$-$C_{12}$ t-alkyl.

Most preferably in formula (I), $R_1$ is methoxy;

$R_2$ is $C_2$-$C_3$ alkyl;

X is O;

$R_3$ is C(=O);

$R_4$ is H or methyl;

$R_5$ is H; and $R_6$ is t-butyl.

The compounds of formula (I) can be made using methods known in the art. Two preferred compounds of formula (I) are 2-{2'-Hydroxy-3'-tert-butyl-5'[3''-(4'''-vinylbenzyloxy)propoxy]phenyl}-5-methoxy-2H-benzotriazole:

and 2-[2'-hydroxy-3'-tert-butyl-5'-(3''-methacryloyloxypropoxy)phenyl]-5-methoxy-2H-benzotriazole The device materials of the present invention comprise a polymerizable yellow dye that attenuates medium- to long-wavelength (430-500 nm) blue light. Many such yellow dyes are known and include, for example, the dye having the structure as well as those described in U.S. Pat. Nos. 7,098,283; 6,878,792; 6,320,008; and 6,310,215. Preferred polymerizable yellow dyes suitable for use in the device materials of the present invention are those of formula (II):

wherein for formula (II)

R' and R" independently are H or $CH_3$;

$R^6$ and $R^7$ independently are H, $C_1$-$C_{20}$ alkyl, $OCH_3$, $OC_2H_5$, $OC_3H_7$, or $OC_4H_9$;

i and j independently are 1 or 2;

$R^8$, $R^9$, $R^{10}$ and $R^{11}$ independently are an acyclic organic spacing group of up to 10 atoms which is composed of carbon, hydrogen, silicon, oxygen, nitrogen, phosphorous, sulfur, chloride, bromine, or fluorine alone or in any combination;

k and m independently are 1 to 6;

l and n independently are 0 to 6;

X is O, NH, $NR^5$; and $R^5 = C_1$ to $C_{10}$ alkyl.

The most preferred compound of formula (II) is N,N-bis-(2-methacroyloxyethyl)-(4-phenylazo)aniline:

Even more preferred are the polymerizable yellow dyes of formula (III):

wherein for formula (III)

R is H or $CH_3$;

$R^1$ is H, $C_1$-$C_{20}$ alkyl, $OCH_3$, $OC_2H_5$, $OC_3H_7$, or $OC_4H_9$;

a and b are independently 1 or 2;

$R^2$ is $R^1$, OH, $NH_2$, $NHR^5$, $N(R^5)_2$, SH, $SR^5$, $OR^5$, $OSi(R^5)_3$, or $Si(R^5)_3$;

$R^3$ is directly attached to the dye moiety and consists of an alkyl group of up to 6 carbon atoms;

$R^4$ is an acyclic organic spacing group of up to 10 atoms which is composed of carbon, hydrogen, silicon, oxygen, nitrogen, phosphorous, sulfur, chloride, bromine, or fluorine alone or in any combination;

X is O, NH, $NR^5$;

$R^5$ is $C_1$ to $C_{10}$ alkyl;

d, e, g, and h independently are an integer from 0 to 4; and c and f independently are an integer from 1 to 4.

The most preferred compound of Formula (III) is N-2-[3-(2'-methylphenylazo)-4-hydroxyphenyl]ethyl methacrylamide:

The polymerizable yellow dyes of formulas (II) and (III) are known and are described in U.S. Pat. No. 5,470,932, the entire contents of which are hereby incorporated by reference.

The ophthalmic device materials of the present invention comprise an amount of the UV absorber of formula (I) and an amount of polymerizable yellow dye to cause the materials to have the required transmission characteristics defined above. In general, the materials will comprise a UV/short wavelength visible light absorber of formula (I) in an amount from 0.5-4%, preferably 1-3%, and most preferably 1.5-2.5%. The materials will generally comprise a polymerizable yellow dye in an amount from 0.001-0.5%, preferably 0.01-0.1%, and most preferably 0.01-0.05%.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula (IV):

wherein:

A is H, $CH_3$, $CH_2CH_3$, or $CH_2OH$;

B is $(CH_2)_m$ or $[O(CH_2)_2]_z$;

C is $(CH_2)_w$;

m is 2-6;

z is 1-10;

Y is nothing, O, S, or NR', provided that if Y is O, S, or NR', then B is $(CH_2)_m$;

R' is H, $CH_3$, $C_{n'}H_{2n'+1}$ (n'=1-10), iso-$OC_3H_7$, $C_6H_5$, or $CH_2C_6H_5$;

w is 0-6, provided that m+w≦8; and

D is H, $C_1$-$C_4$ alkyl, $C_1$-$C_4$ alkoxy, $C_6H_5$, $CH_2C_6H_5$ or halogen.

Preferred monomers of formula (IV) are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula (IV) are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

The materials of the present invention generally comprise a total of at least about 75%, preferably at least about 80%, of device-forming monomers.

In addition to a device-forming monomer, a UV absorber of formula (I), and a polymerizable yellow dye, the device materials of the present invention comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—$(CH_2CH_2O)_p$—$C$(=O)$C(CH_3)$=$CH_2$ where p=1-50; and $CH_2$=$C(CH_3)C$(=O)O$(CH_2)_tO$—$C$(=O)$C(CH_3)$=$CH_2$ where t=3-20; and their corresponding acrylates. A preferred cross-linking monomer is $CH_2$=$C(CH_3)C$(=O)O—$(CH_2CH_2O)_p$—$C$(=O)$C(CH_3)$=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for the device materials of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

Preferably, the ingredients and their proportion are selected so that the device materials of the present invention possess the following properties, which make the materials of the present invention particularly suitable for use in IOLs which are to be inserted through incisions of 4 mm or less. For convenience, the device materials may be referred to as lens materials.

The lens material preferably has a refractive index in the dry state of at least about 1.50 as measured by an Abbe' refractometer at 589 nm (Na light source). For a given optic diameter, optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the lens material, which affects the material's folding and unfolding characteristics, is preferably below about 25° C., and more preferably below about 15° C. Tg is measured by differential scanning calorimetry at 10° C./min., and is determined as the half-height of the heat capacity increase.

The lens material will have an elongation (strain at break) of at least 75%, preferably at least 90%, and most preferably at least 100%. This property indicates that the lens generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using a tensile tester. The grip distance is set at 11 mm and a crosshead speed is set at 500 mm/minute and the sample is pulled to failure. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 25% secant modulus is calculated as the slope of a straight line drawn on the stress-strain curve between 0% strain and 25% strain. The 100% secant modulus is calculated as the slope of a straight line drawn on the stress-strain curve between 0% strain and 100% strain.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic devices such as contact lenses, keratoprostheses, and corneal inlays or rings.

The invention will be further illustrated by the following examples, which are intended to be illustrative, but not limiting.

EXAMPLE 1

Acrylic device materials containing 2-[2'-hydroxy-3'-tert-butyl-5'-(3"-methacryloyloxypropoxy)phenyl]-5-methoxy-2H-benzotriazole ("UV13") in combination with N-2-[3-(2'-methylphenylazo)-4-hydroxyphenyl] ethyl methacrylamide ("AL8739")

A monomer diluent formulation of 60 grams consisting of 2-phenylethyl acrylate (PEA), 2-phenylethyl methacrylate (PEMA), and 1,4-butanediol diacrylate (BDDA) was prepared by mixing the three monomers together in the proportions of 65:30:3.2 parts by weight. A 2.5% UV absorber stock formulation was prepared by dissolving 0.5 grams of UV13 into 19.5 grams of PEA/PEMA/BDDA formulation. Finally, a second stock formulation containing 0.25% of AL8739 was prepared by dissolving 0.25 grams of AL8739 into 9.75 grams of the PEA/PEMA/BDDA formulation.

Seventeen PEA/PEMA/BDDA formulations containing 0.2 to 2% UV13 with 0.01-0.04% AL8739 and one control with no AL8739 (17) were prepared by mixing two stock formulations with PEA/PEMA/BDDA diluent formulation in the proportions provided in Table 2.

TABLE 2

Preparation scheme of PEA/PEMA Formulations of UV13 in combination with AL8739.

| Solution No. | Grams of Stock UV13 | Grams of Stock AL8739 | Grams of PEA/ PEMA/ BDDA | Target Conc, wt % UV13 | Target Conc wt % AL8739 | Actual Wt. UV13 Stock 2.50% | Actual Wt. AL8739 Stock 0.25% | Actual wt PEA/ PEMA/ BDDA Stock | Actual Conc, wt % UV13 | Actual Conc, wt % AL8739 |
|---|---|---|---|---|---|---|---|---|---|---|
| 1 | 1.60 | 0.08 | 0.32 | 2 | 0.01 | 1.6027 | 0.0799 | 0.3198 | 2 | 0.01 |
| 2 | 1.60 | 0.16 | 0.24 | 2 | 0.02 | 1.6021 | 0.1605 | 0.2405 | 2 | 0.02 |
| 3 | 1.60 | 0.24 | 0.16 | 2 | 0.03 | 1.6007 | 0.2403 | 0.1603 | 2 | 0.03 |
| 4 | 1.60 | 0.32 | 0.08 | 2 | 0.04 | 1.6024 | 0.3207 | 0.0803 | 2 | 0.04 |
| 5 | 0.80 | 0.08 | 1.12 | 1 | 0.01 | 0.8016 | 0.0804 | 1.1209 | 1 | 0.01 |
| 6 | 0.80 | 0.16 | 1.04 | 1 | 0.02 | 0.8033 | 0.1602 | 1.0418 | 1 | 0.02 |
| 7 | 0.80 | 0.24 | 0.96 | 1 | 0.03 | 0.8036 | 0.2406 | 0.9617 | 1 | 0.03 |
| 8 | 0.80 | 0.32 | 0.88 | 1 | 0.04 | 0.8041 | 0.3204 | 0.8806 | 1 | 0.04 |
| 9 | 0.40 | 0.08 | 1.52 | 0.5 | 0.01 | 0.4016 | 0.0805 | 1.5217 | 0.5 | 0.01 |
| 10 | 0.40 | 0.16 | 1.44 | 0.5 | 0.02 | 0.4021 | 0.1612 | 1.4412 | 0.5 | 0.02 |
| 11 | 0.40 | 0.24 | 1.36 | 0.5 | 0.03 | 0.4000 | 0.2417 | 1.3597 | 0.5 | 0.03 |
| 12 | 0.40 | 0.32 | 1.28 | 0.5 | 0.04 | 0.4008 | 0.3206 | 1.2798 | 0.5 | 0.04 |
| 13 | 0.16 | 0.08 | 1.76 | 0.2 | 0.01 | 0.1601 | 0.0813 | 1.7604 | 0.2 | 0.01 |
| 14 | 0.16 | 0.16 | 1.68 | 0.2 | 0.02 | 0.1599 | 0.1608 | 1.6803 | 0.2 | 0.02 |
| 15 | 0.16 | 0.24 | 1.60 | 0.2 | 0.03 | 0.1604 | 0.2398 | 1.6014 | 0.2 | 0.03 |
| 16 | 0.16 | 0.32 | 1.52 | 0.2 | 0.04 | 0.1598 | 0.3215 | 1.5208 | 0.2 | 0.04 |
| 17 | 1.60 | 0 | 0.40 | 2 | 0 | 1.6002 | 0 | 0.4000 | 2.0 | 0 |

Figure 1:
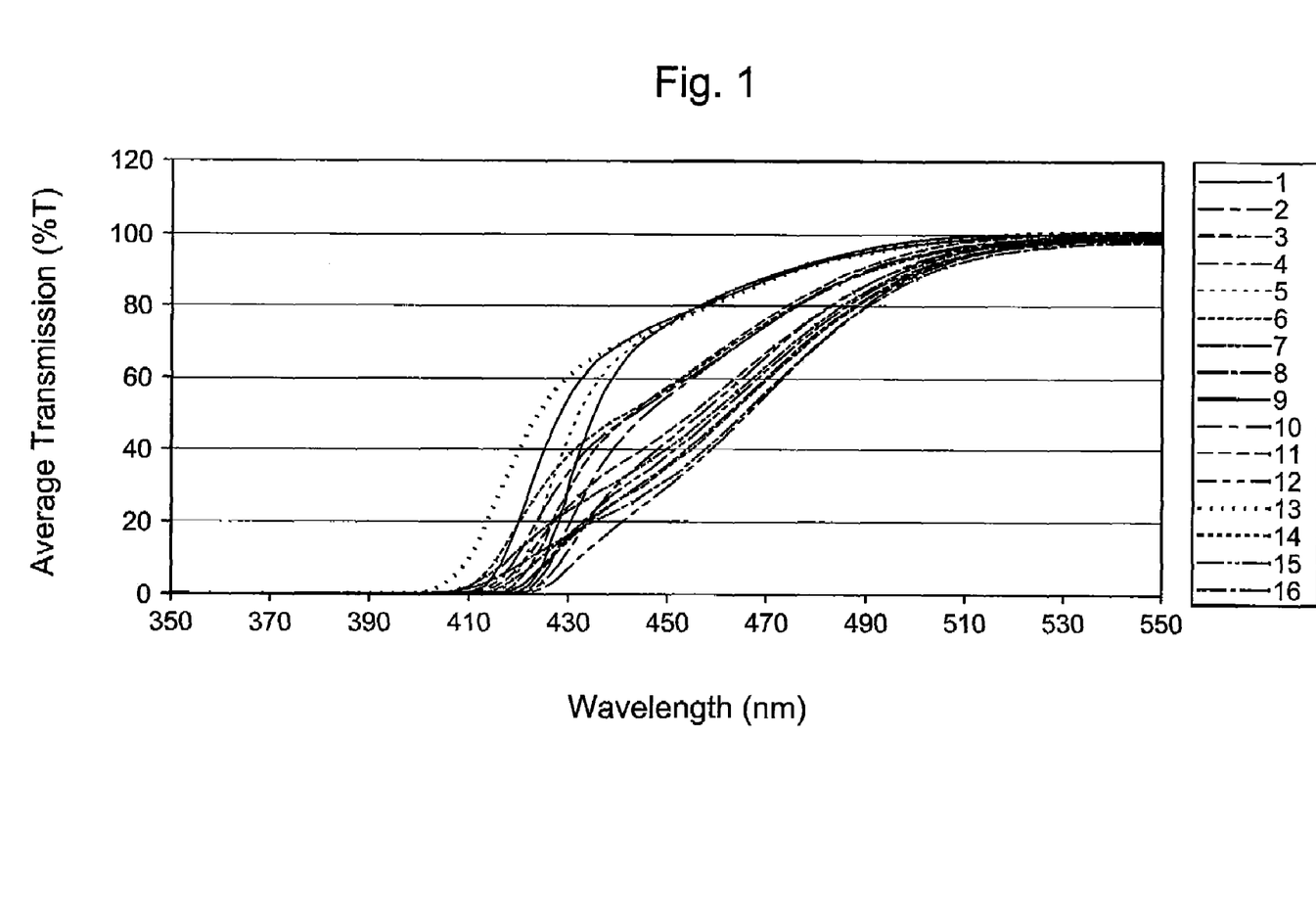
FIGS. 1 and 2 show the transmittance of the ophthalmic device materials of Examples 1 and 2.

Each formulation was analyzed by UV-Visible transmission spectroscopy in a 1-mm pathlength quartz cell, which provides a reasonable correlation to IOL central thickness, using a Perkin-Elmer Lambda 35 instrument. After performing a background correction with the PEA/PEMA/BDDA formulation, each of the 16 formulations was analyzed from 300 to 800 nm. The transmission spectra obtained are shown in FIG. 1.

To each formulation was added 0.5% bis-(4-tert-butylcyclohexylperoxy) dicarbonate (Perkadox-16, Akzo Corp.) initiator, which was dissolved by vortex mixing. After mixing, each formulation was passed through a 0.2 μm membrane filter and purged with nitrogen. Finally, each formulation was cast into polypropylene molds to form 1×2-cm×~1-mm rectangular films ("slab") by curing at 80° C. for 1 hour, 90° C. for 1 hour and 100° C. for 1 hour in a programmable temperature oven.

After curing the films were demolded and placed into labeled polypropylene tissue capsules for further processing. The film samples were Soxhlet extracted with acetone, dried in air and dried at 60° C. under vacuum (<0.1 inches of Hg) to remove residual acetone.

EXAMPLE 2

Comparison Example of 2% UV13 and 2% OMTP with Varying Levels of AL8739 Chromophore This example provides a comparison of the conventional benzotriazole UV absorber, oMTP (ortho-methallyl Tinuvin P), with a UV/short wavelength visible light absorber of the type specified in for the materials of the present invention. Another stock 2.56% OMTP solution was prepared by dissolving 0.250 grams of OMTP into 9.752 grams of the PEA/PEMA/BDDA monomer diluent described above in Example 1. The stock formulation solution containing 0.25% AL8739 polymerizable yellow dye was also employed in preparing comparative formulations as described below.

Five oMTP formulations were prepared containing 2% OMTP with 0, 0.01, 0.02, 0.03 and 0.04% AL8739 polymerizable yellow dye by combining the stock formulation solutions according to the scheme provided in Table 3.

TABLE 3

Preparation scheme of PEA/PEMA Formulations of oMTP in combination with AL8739 blue light chromophore

| Solution No. | Grams of Stock oMTP | Grams of Stock AL8739 | Grams of PEA/ PEMA/ BDDA | Target Conc, wt % oMTP | Target Conc wt % AL8739 | Actual Wt. oMTP Stock 2.50% | Actual Wt. AL8739 Stock 0.25% | Actual wt PEA/ PEMA/ BDDA Stock | Actual Conc, wt % oMTP | Actual Conc, wt % AL8739 |
|---|---|---|---|---|---|---|---|---|---|---|
| 1 | 1.60 | 0.08 | 0.32 | 2 | 0.01 | 1.6003 | 0.0796 | 0.3208 | 2 | 0.01 |
| 2 | 1.60 | 0.16 | 0.24 | 2 | 0.02 | 1.6014 | 0.1610 | 0.2412 | 2 | 0.02 |
| 3 | 1.60 | 0.24 | 0.16 | 2 | 0.03 | 1.6009 | 0.2398 | 0.1609 | 2 | 0.03 |
| 4 | 1.60 | 0.32 | 0.08 | 2 | 0.04 | 1.6012 | 0.3207 | 0.0810 | 2 | 0.04 |
| 5 | 0.80 | 0.08 | 1.12 | 1 | 0 | 0.8018 | 0 | 0.4011 | 2 | 0 |

To each formulation was added 0.5% bis-(4-tert-butylcyclohexylperoxy)dicarbonate (Perkadox-16, Akzo Corp.) initiator, which was dissolved by vortex mixing. After mixing, each formulation was passed through a 0.2 μm membrane filter and purged with nitrogen. Finally, each formulation was cast into polypropylene molds to form 1×2-cm×~1-mm rectangular films by curing at 80° C. for 1 hour, 90° C. for 1 hour and 100° C. for 1 hour in a programmable temperature oven.

After curing the films were demolded and placed into labeled polypropylene tissue capsules for further processing. The film samples were Soxhlet extracted with acetone, dried in air and dried at 60° C. under vacuum (<0.1 inches of Hg) to remove residual acetone. After extraction and vacuum drying, film samples were analyzed by UV-Visible transmission spectroscopy from 300-800 nm using a Perkin-Elmer Lambda 35 instrument equipped with a Lab Sphere RSA-PE-20 integrating sphere. Similarly the films 1-4 and 17 from Example 1 were also analyzed by UV-Visible spectroscopy for comparison.

Figure 2:
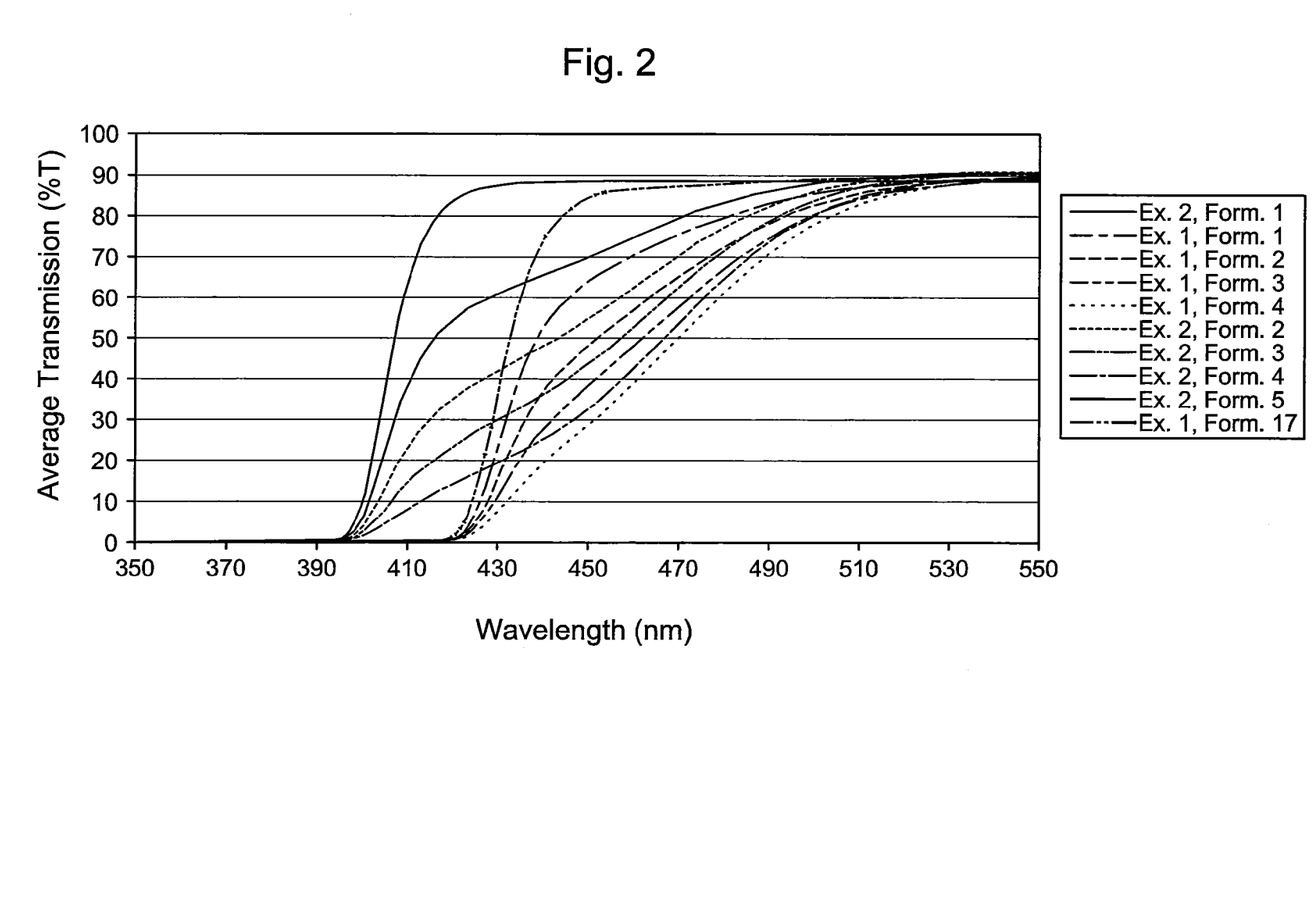

The results are shown in FIG. 2, which provides a spectral comparison of Formulations 1-4 and 17 of Example 1 and 1-5 of Example 2. Table 4 provides the wavelengths for 1% and 10% UV cut-off from the transmission data in FIG. 2. It is clear that a conventional benzotriazole UV absorber, like OMTP, does not provide a significant cut-off in the short wavelength visible region (410-430 nm) as compared to a UV/short wavelength visible light absorber of formula (I), like UV13. The overall attenuation of the blue light from 400-500 nm is maintained by the addition of the AL8739 polymerizable yellow dye and is indicated by the % T values provided at 450 nm.

The 1% cut-offs for all the Example 1 (UV13 & AL8739) formulations 1-4 are between 421-423 nm and the 10% cut-offs range from 426.5 to 432 nm. In contrast, in the Example 2 (OMTP & AL8739) formulations 1-4, the 1% cut-offs for formulations 1-4 range from 396.5 to 399 nm and the 10% cut-offs range from 401.5 to 413 nm. This comparison demonstrates the improved cut-offs in the short wavelength visible light region (410-430) achieved by the UV13 formulations (Example 1) relative to the OMTP formulations (Example 2). The 450 nm transmission is an indicator of blue light attenuation and the difference between the UV13 and OMTP formulations is about 6% T for each different AL8739 concentration.

TABLE 4

Comparison of UV-Vis Data of Formulations from Examples 1 and 2

| Example | Formulation No. | UV Absorber Name | AL8739 Conc. (wt %) | UV Cutoff (nm) 1% T | 10% T | % T at 450 nm |
|---|---|---|---|---|---|---|
| 1 | 1 | UV13 | 0.01 | 421 | 426.5 | 63.91 |
|   | 2 |   | 0.02 | 421.5 | 428 | 47.99 |
|   | 3 |   | 0.03 | 422 | 429.5 | 38.06 |
|   | 4 |   | 0.04 | 423 | 432 | 28.45 |
|   | 17 |   | 0 | 419.5 | 424.5 | 84.05 |
| 2 | 1 | oMTP | 0.01 | 396.5 | 401.5 | 69.89 |
|   | 2 |   | 0.02 | 397.5 | 404 | 54.62 |
|   | 3 |   | 0.03 | 398 | 406.5 | 43.36 |
|   | 4 |   | 0.04 | 399 | 413 | 32.41 |
|   | 5 |   | 0 | 395.5 | 400 | 88.40 |

(UV Absorber Conc: 2 wt% for all rows)

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. An ophthalmic device material comprising
a) a UV/short wavelength visible light absorber of formula (I)

wherein for formula (I)

$R_1$ is a halogen, OH, $C_1$-$C_{12}$ alkyloxy, optionally substituted phenoxy, or optionally substituted napthyloxy, where the optional substituents are $C_1$-$C_6$ alkyl, $C_6$-$C_6$ alkoxy, OH, —$(CH_2CH_2O)_n$—, or —$(CH_2CH(CH_3)O)_n$—;

$R_2$ is a $C_1$-$C_{12}$ alkyl, $(CH_2CH_2O)_n$, $(CH_2CH(CH_3)O)_n$, or
$CH_2CH_2CH_2(Si(CH_3)_2O)_mSi(CH_3)_2CH_2CH_2CH_2$;

X is nothing if $R_2$ is $(CH_2CH_2O)_n$ or $(CH_2CH(CH_3)O)_n$, otherwise X is O, $NR_4$, or S;

$R_3$ is nothing, C(=O), C(=O)$C_jH_{2j}$, $C_1$-$C_6$ alkyl, phenyl, or $C_1$-$C_6$ alkylphenyl;

$R_4$ is H or methyl;

$R_5$ is H, $C_1$-$C_6$ alkyl, or phenyl;

$R_6$ is H or $C_1$-$C_{12}$ alkyl;

n is 2-10; and j is 1-6;

b) a polymerizable yellow dye that attenuates light having wavelengths in the range 430-500 nm wherein the polymerizable yellow dye is selected from the group consisting of dyes of formula (II): dyes of formula (III); and -continued (II)

wherein for formula (II)
R' and R" independently are H or $CH_3$;
$R^6$ and $R^7$ independently are H, $C_1$-$C_{20}$ alkyl, $OCH_3$, $OC_2H_5$, $OC_3H_7$, or $OC_4H_9$;
i and j independently are 1 or 2;
$R^8$ and $R^9$, $R^{10}$ and $R^{11}$ independently are an acyclic organic spacing group of up to 10 atoms which is composed of carbon, hydrogen, silicon, oxygen, nitrogen, phosphorous, sulfur, chloride, bromine, or fluorine alone or in any combination;
k and m independently are 1 to 6;
l and n independently are 0 to 6;
X is O, NH, $NR^5$; and
$R^5$=$C_1$ to $C_{10}$ alkyl;

(III)

wherein for formula (III)
R is H or $CH_3$;
$R^1$ is H, $C_1$-$C_{20}$ alkyl, $OCH_3$, $OC_3H_7$, or $OC_4H_9$;
a and b are independently 1 or 2;
$R^2$ is $R^1$, OH, $NH_2$, $NHR^5$, $N(R^5)_2$, SH, $SR^5$, $OR^5$, $OSi(R^5)_3$, or $Si(R^5)_3$;
$R^3$ is directly attached to the dye moiety and consists of an alkyl group of up to 6 carbon atoms;
$R^4$ is an acyclic organic spacing group of up to 10 atoms which is composed of carbon, hydrogen, silicon, oxygen, nitrogen, phosphorous, sulfur, chloride, bromine, or fluorine alone or in any combination;
X is O, NH, $NR^5$;
$R^5$ is $C_1$ to $C_{10}$ alkyl;
d, e, g, and h independently are an integer from 0 to 4; and
c and f independently are an integer from 1 to 4;
and wherein the amount of UV/short wavelength visible light absorber is from 1-3% (wt.) and the amount of polymerizable yellow dye is from 0.01-0.1% (wt.);
c) a device-forming monomer in an amount of 75% (wt.) or more; and
d) a cross-linking agent, wherein the amount of the UV/short wavelength visible light absorber and the amount of the polymerizable yellow dye are sufficient to cause the ophthalmic device material to have the following light transmission characteristics:

| Blue light region | Transmission Characteristic | Ranges of Transmission Characteristics* | |
|---|---|---|---|
| | | Minimum value | Maximum value |
| Blue-violet cutoff | 1% T | 410 nm | 430 nm |
| | 10% T | 420 nm | 440 nm |
| Mid-blue transition region | 440 nm | 10% T | 75% T |
| | 450 nm | 28% T | 80% T |
| | 460 nm | 40% T | 85% T |
| High transmission blue light region | 470 nm | 55% T | 95% T |
| | 480 nm | 68% T | 95% T |
| | 490 nm | 80% T | 95% T |
| | 500 nm | 85% T | 95% T. |

*determined by UV-Visible measurements in air.

2. The ophthalmic device material of claim 1 wherein in formula (I)
$R_1$ is Cl, Br, $C_1$-$C_4$ alkoxy, or phenoxy;
$R_2$ is $C_1$-$C_6$ alkyl;
X is O or $NR_4$;
$R_3$ is C(=O) or $C_1$-$C_6$ alkylphenyl;
$R_4$ is H or methyl;
$R_5$ is H; and
$R_6$ is $C_4$-$C_{12}$ t-alkyl.

3. The ophthalmic device material of claim 2 wherein in formula (I)
$R_1$ is methoxy;
$R_2$ is $C_2$-$C_3$ alkyl;
X is O;
$R_3$ is C(=O);
$R_4$ is H or methyl;
$R_5$ is H; and
$R_6$ is t-butyl.

4. The ophthalmic device material of claim 1 wherein the UV/short wavelength visible light absorber of formula (I) is selected from the group consisting of 2-{2'-Hydroxy-3'-tert-butyl-5'[3"-(4'"-vinylbenzyloxy)propoxy]phenyl}-5-methoxy-2H-benzotriazole and 2-[2'-hydroxy-3'-tert-butyl-5'-(3"-methacryloyloxypropoxy)phenyl]-5-methoxy-2H-benzotriazole.

5. The ophthalmic device material of claim 1 wherein the polymerizable yellow dye is selected from the group consisting of N,N-bis- (2-methacroyloxyethyl)-(4-phenylazo)aniline and N-2-[3-(2'-methylphenylazo)-4-Hydroxyphenyl]ethyl methacrylamide.

6. The ophthalmic device material of claim 1 wherein the amount of UV/short wavelength visible light absorber is from 1.5-2.5% (wt.).

7. The ophthalmic device material of claim 1 wherein the amount of polymerizable yellow dye is from 0.01-0.05% (wt.).

8. The ophthalmic device material of claim 1 wherein the device-forming monomer is selected from the group consisting of acrylic and silicone-containing monomers.

9. The ophthalmic device material of claim 8 wherein the device-forming monomer is a monomer of formula (IV)

wherein for formula (IV):
A is H, CH$_3$, CH$_2$CH$_3$, or CH$_2$OH;
B is (CH$_2$)$_m$ or [O(CH$_2$)$_2$]$_z$;
C is (CH$_2$)$_w$;
m is 2-6;
z is 1-10;
Y is nothing, O, S, or NR', provided that if Y is O, S, or NR', then B is (CH$_2$)$_m$;
R' is H, CH$_3$, C$_{n'}$H$_{2n'+1}$ (n'=1-10), iso-OC$_3$H$_7$, C$_6$H$_5$, or CH$_2$C$_6$H$_5$;
w is 0-6, provided that m+w≦8; and
D is H, C$_1$-C$_4$ alkyl, C$_1$-C$_4$ alkoxy, C$_6$H$_5$, CH$_2$C$_6$H$_5$ or halogen.

10. The ophthalmic device material of claim 9 wherein for formula (IV)
A is H or CH$_3$, B is (CH$_2$)$_m$, m is 2-5, Y is nothing or O, w is 0-1, and D is H.

11. The ophthalmic device material of claim 10 wherein the device-forming monomer is selected from the group consisting of 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

12. The ophthalmic device material of claim 1 wherein the cross-linking agent is selected from the group consisting of ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; CH$_2$=C(CH$_3$)C(=O)O—(CH$_2$CH$_2$O)$_p$-C(=O)C(CH$_3$)=CH$_2$ where p=1-50; and CH$_2$=C(CH$_3$)C(=O)O(CH$_2$)$_t$O—C(=O)C(CH$_3$)=CH$_2$ where t=3-20; and their corresponding acrylates.

13. The ophthalmic device material of claim 1 wherein the amount of cross-linking agent is 0.1-20% (wt.).

14. An ophthalmic device comprising the material of claim 1 wherein the ophthalmic device is selected from the group consisting of intraocular lenses; contact lenses; keratoprostheses; or corneal rings or inlays.

15. The ophthalmic device material of claim 1 wherein R$_1$ is OH, C$_1$-C$_{12}$ alkyloxy, optionally substituted phenoxy, or optionally substituted napthyloxy, where the optional substituents are C$_1$-C$_6$ alkyl, C$_1$-C$_6$ alkoxy, OH, —(CH$_2$CH$_2$O)$_n$—, or —(CH$_2$CH(CH$_3$)O)$_n$—.

16. The ophthalmic device material of claim 1 wherein the device material has an elongation (strain at break) of at least 100% and the glass transition temperature of the device material is below about 15° C.

* * * * *

UNITED STATES PATENT AND TRADEMARK OFFICE
CERTIFICATE OF CORRECTION

PATENT NO. : 7,691,918 B2
APPLICATION NO. : 11/871411
DATED : April 6, 2010
INVENTOR(S) : David L. Jinkerson, Joseph I. Weinschenk, III and Mutlu Karakelle It is certified that error appears in the above-identified patent and that said Letters Patent is hereby corrected as shown below:

Claim 1, column 12, line 32 delete "$C_6$-$C_6$ alkoxy" and insert --$C_1$-$C_6$ alkoxy--.

Claim 1, column 13, line 42 insert --$OC_2H_5$,-- after $OCH_3$,.

Signed and Sealed this

Eighteenth Day of May, 2010

David J. Kappos
*Director of the United States Patent and Trademark Office*